(12) United States Patent
Tekulve et al.

(10) Patent No.: US 8,702,746 B2
(45) Date of Patent: Apr. 22, 2014

(54) DEVICE AND METHOD FOR OCCLUSION OF FLUID FLOW THROUGH A BODY VESSEL

(75) Inventors: Kurt J. Tekulve, Ellettsville, IN (US); Andrew W. Conder, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1495 days.

(21) Appl. No.: 12/111,474

(22) Filed: Apr. 29, 2008

(65) Prior Publication Data
US 2009/0270908 A1  Oct. 29, 2009

(51) Int. Cl.
*A61M 29/00*  (2006.01)

(52) U.S. Cl.
USPC .......................................... 606/200

(58) Field of Classification Search
USPC .................. 606/200; 128/830–841
See application file for complete search history.

(56) References Cited

U.S. PATENT DOCUMENTS

| | | | |
|---|---|---|---|
| 5,413,586 A | 5/1995 | Dibie et al. | |
| 5,639,277 A | 6/1997 | Mariant et al. | |
| 5,649,949 A | 7/1997 | Wallace et al. | |
| 5,749,891 A | 5/1998 | Ken et al. | |
| 5,833,705 A | 11/1998 | Ken et al. | |
| 5,980,514 A | 11/1999 | Kupiecki et al. | |
| 6,033,423 A * | 3/2000 | Ken et al. | 606/200 |
| 6,053,924 A | 4/2000 | Hussein | |
| 6,063,111 A | 5/2000 | Hieshima et al. | |
| 6,203,547 B1 | 3/2001 | Nguyen et al. | |
| 6,634,361 B1 | 10/2003 | Nikolchev et al. | |
| 6,763,833 B1 | 7/2004 | Khera et al. | |
| 6,802,851 B2 | 10/2004 | Jones et al. | |
| 6,849,081 B2 * | 2/2005 | Sepetka et al. | 606/213 |
| 7,153,323 B1 | 12/2006 | Teoh et al. | |
| 7,166,122 B2 | 1/2007 | Aganon et al. | |
| 2005/0004598 A1 | 1/2005 | White, Jr. et al. | |
| 2005/0107823 A1* | 5/2005 | Leone et al. | 606/200 |
| 2006/0052816 A1* | 3/2006 | Bates et al. | 606/200 |
| 2006/0079926 A1* | 4/2006 | Desai et al. | 606/200 |
| 2006/0116711 A1* | 6/2006 | Elliott et al. | 606/200 |

\* cited by examiner

*Primary Examiner* — Katherine Dowe (74) *Attorney, Agent, or Firm* — Brinks Gilson & Lione (57) ABSTRACT

The present invention provides an improved occluding device and an improved method of occluding fluid through a body vessel. The occluding device comprises an inner coil. At least one outer coil is disposed about a portion of the inner coil. The outer coil has a pre-curled tension to facilitate the outer coil to be curled within the lumen of the body vessel when deployed.

21 Claims, 5 Drawing Sheets

DEVICE AND METHOD FOR OCCLUSION OF FLUID FLOW THROUGH A BODY VESSEL

BACKGROUND OF THE INVENTION

1. Field of the Invention

The present invention relates to medical devices. More particularly, the invention relates to occluding devices and methods of occluding fluid flow through a body vessel.

2. Background

Pushable coils (e.g. pushable fibered coils) have been used as a primary occluding device for treatment of various arteriovenous malformations (AVM) and varicoceles, as well as for many other arteriovenous abnormalities in the body. Occluding devices are also used to repair abnormal shunts between arteries and veins, prevent or reduce blood flow to tumors, stop hemorrhaging as a result of trauma, and stabilize aneurysms to prevent rupture. Pushable coils may be configured in a variety of sizes with varying diameters and may be made of several different materials including stainless steel and platinum. Occlusion devices may vary for differing purposes, e.g., to hold the device in place within a cavity or vessel and to pack the device within the vessel for enhanced occlusion.

Although current pushable coils are adequate, such coils may be improved for more effective occlusion of fluid flow through a lumen of a body vessel. Many medical procedures for occluding blood flow through an artery or vein require a number of coils, since a single coil or two may not be sufficient to effectively occlude blood flow through a lumen of an artery or vein. This is particularly the case when occlusion of a high blood flow body vessel is necessary, such as for example, a major artery. In many current procedures, numerous coils are packed within each other to produce effective cross-sectional occlusion of fluid flow through the body vessel. In some instances, these procedures may involve an undesirable amount of additional time and cost.

BRIEF SUMMARY OF THE INVENTION

The present invention provides an improved occluding device and an improved method of occluding fluid through a body vessel. The occluding device comprises an inner coil. At least one outer coil is disposed about a portion of the inner coil. The outer coil has a first pre-curled tension to facilitate the outer coil to be curled within the lumen of a body vessel when deployed.

In one aspect, the inner coil has a second pre-curled tension to facilitate the outer coil to be curled within the lumen of a body vessel when deployed.

The present invention further includes an improved embolization kit for occluding fluid flow through a body vessel. The kit comprises the occluding device described in the foregoing paragraph as well as a guide catheter. A microcatheter is configured to be passed through the guide catheter to position the microcatheter in the body vessel and to deploy the occluding device.

The present invention also includes an improved method for occluding fluid flow through a body vessel. The method comprises deploying an occluding device into a lumen of the body vessel. The occluding device includes an inner coil and at least one outer coil disposed about a portion of the inner coil. The outer coil has a pre-curled tension to facilitate the outer coil to be curled. Deploying the occluding device includes deploying the outer coil at a desired point of occlusion in the body vessel. The outer coil curls to hold the occluding device in place within the body vessel. The inner coil is deployed across the lumen of the body vessel adjacent to the outer coil to pack the outer coil and occlude the body vessel.

Further objects, features, and advantages of the present invention will become apparent from consideration of the following description and the appended claims when taken in connection with the accompanying drawings.

BRIEF DESCRIPTION OF THE DRAWINGS

FIG. 1b is a cross-sectional view of the occluding device depicted in FIG. 1a;

FIG. 3b is a cross-sectional view of the occluding device depicted in FIG. 3a;

DETAILED DESCRIPTION OF THE INVENTION

The following provides a detailed description of currently preferred embodiments of the present invention. The description is not intended to limit the invention in any manner, but rather serves to enable those skilled in the art to make and use the invention.

The present invention generally provides an occluding device used for transcatheter embolization. The occluding device has multiple coils configured to provide better attachment of the device to an inner wall of a body vessel and improved occlusion of fluid flow through the vessel. The occluding device is preferably used to occlude fluid flow through a body vessel due to a blood vessel malformation occurring in the brain, like aneurysms, or another part of the body. The occluding device comprises an outer coil having a pre-curled tension and an inner coil. The outer coil is disposed about a portion of the inner coil. In one aspect, the outer coil has greater rigidity than the inner coil. Preferably, the outer coil forms a helical shape or other curled configuration within the body vessel so as to anchor the occluding device against the inner wall of the body vessel. The inner coil preferably is deployed across the lumen of the body vessel adjacent to the outer coil so as to pack the outer coil and occlude the body vessel. To further facilitate occlusion of fluid flow, the occluding device may have fibers extending therefrom.

The occluding device may also be used for treatment of renal arteriovenous malfunction (AVM), pulmonary AVM, vascular tumors, low-flow fistulas, trauma related hemorrhages, and visceral vasculature defects including varicoceles, aneurysms, and selected telangiectasias. For example, treatment of visceral vasculature defects may include but are not limited to embolotherapy on gastroduogenal hemorrhages, hepatic aneurysms, celiac aneurysms, internal iliac aneurysms, and internal spermatic varicoceles.

Figure 1A:
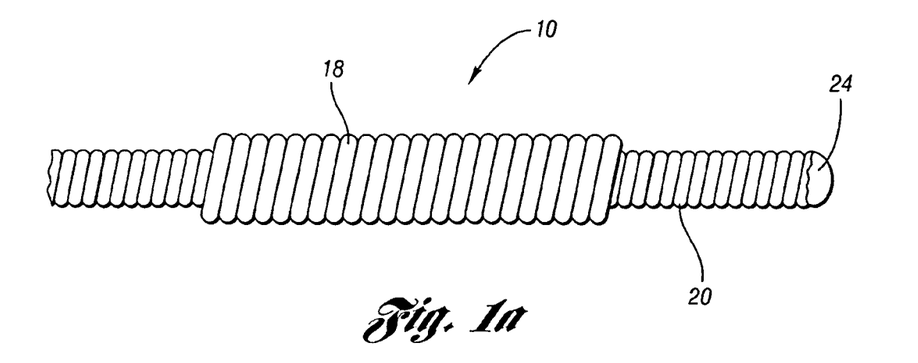
FIG. 1a is a side view of an occluding device in accordance with one embodiment of the present invention.
Figure 1B:
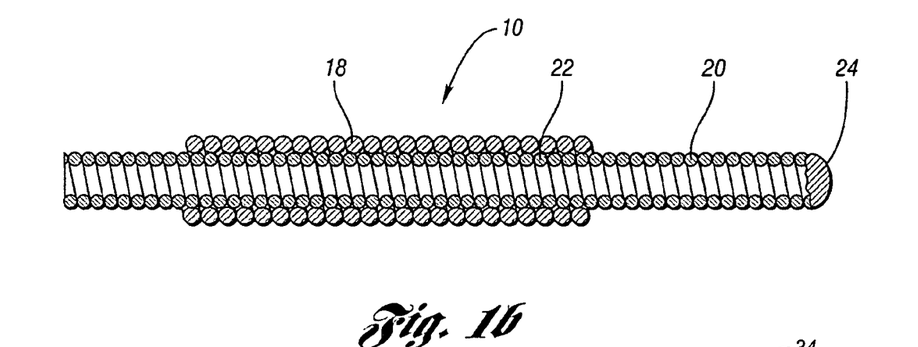
Figure 2:
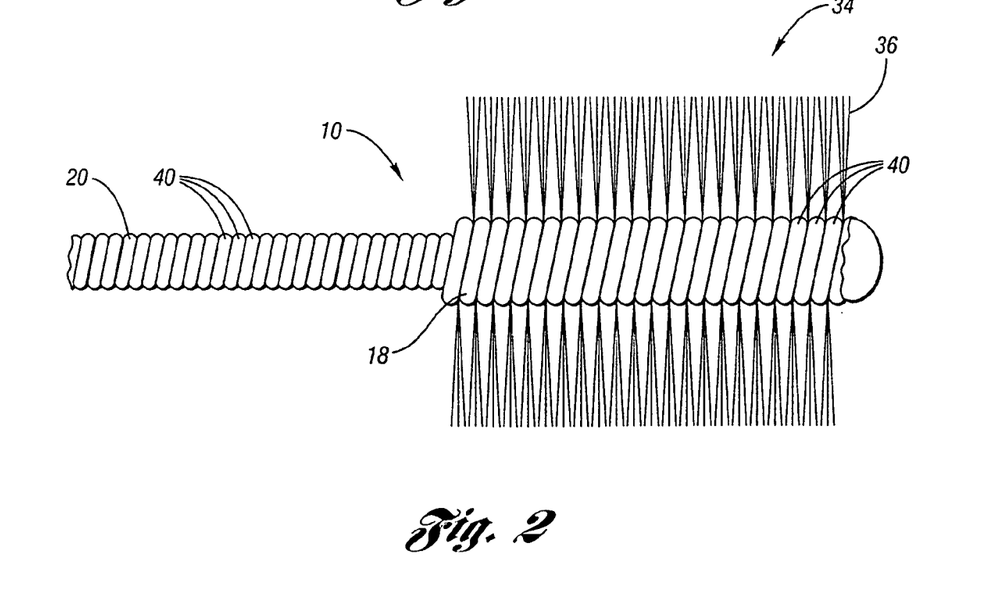
FIG. 2 is a side view of an occluding device in accordance with another embodiment of the present invention.
Figures 4, 5A, 5B, 5C, 5D:
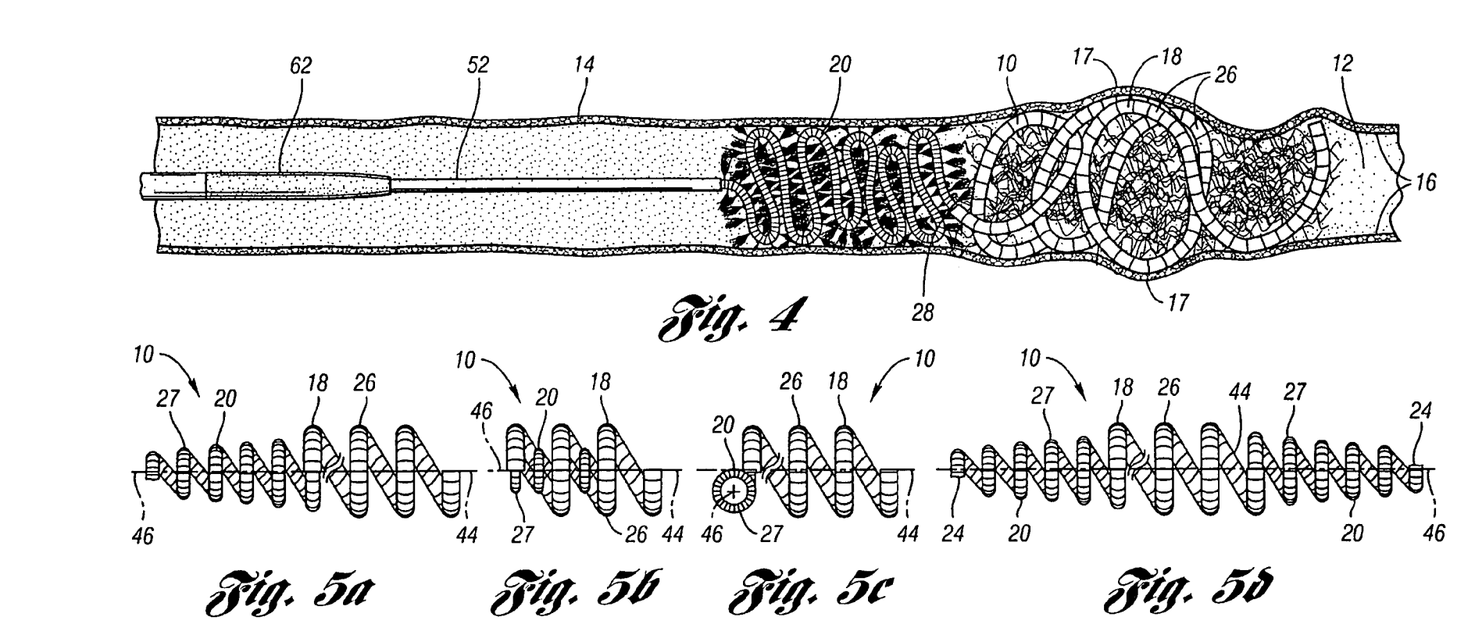
FIG. 4 is a cross-sectional environmental view of an occluding device deployed in a body vessel.
FIG. 5a is a side view of an occluding device in accordance with another embodiment of the present invention.
FIG. 5b is a side view of an occluding device in accordance with yet another embodiment of the present invention.
FIG. 5c is a side view of an occluding device in accordance with an embodiment of the present invention.
FIG. 5d is a side view of an occluding device in accordance with another embodiment of the present invention.

Referring to FIGS. 1a, 1b and 4, at least one embodiment of an occluding device in accordance with the present invention is provided. FIG. 4 illustrates an occluding device 10 in a deployed state for occlusion of fluid flow through a lumen 12 of a body vessel 14. As shown, the occluding device 10 is positioned to engage an inner wall 16 of the body vessel 14 and comprises an outer coil 18 and an inner coil 20. The outer coil 18 is disposed about a portion 22 (see FIG. 1b) of the inner coil 20. The portion 22 may be disposed between opposing ends 24 of the inner coil as illustrated in FIGS. 1a and 1b. Alternatively, the portion 22 may include one of the ends 24 of the inner coil 20 (see FIG. 2 illustrating the outer coil 18 disposed over one end of the inner coil 20).

The outer coil 18 has a pre-curled tension to facilitate the outer coil 20 being curled within the body vessel 14 (see FIG. 4). In one example, the outer coil 18 curls to form a series of loops 26 within the body vessel 14. The series of loops 26 define a cross-sectional area formed axially along the outer coil 18. Preferably, the cross-sectional area formed by the outer coil 18 is greater than a cross-sectional area of the body vessel 14. In this scenario, the outer coil 18 pushes against the inner wall 16 (depicted as the outwardly bulging vessel wall 17 in FIG. 4) so as to anchor itself within the body vessel 14.

Figure 3A:
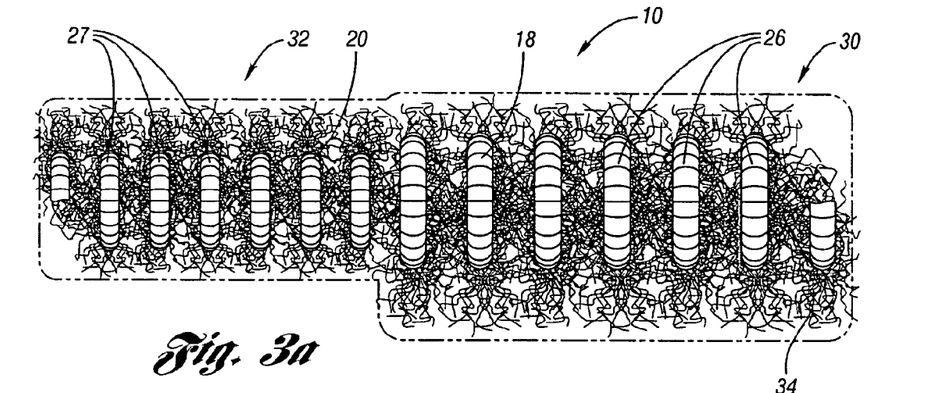
FIG. 3a is a side view of an occluding device in accordance with yet another embodiment of the present invention.
Figure 3B:
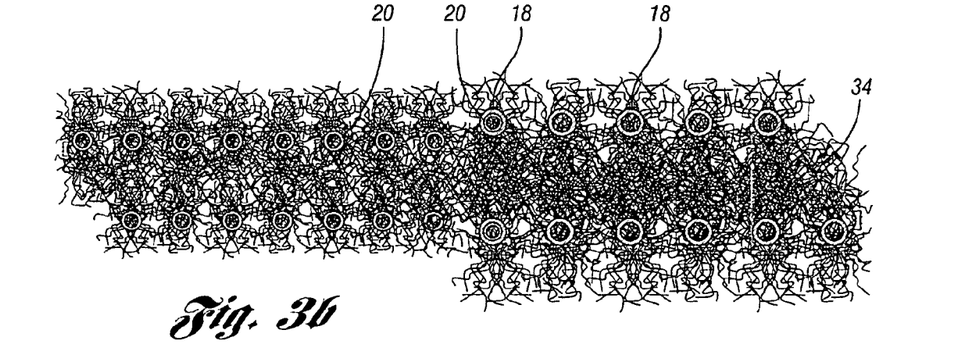

Referring to FIGS. 3a, 3b and 4, the inner coil 20 may have a pre-curled tension to facilitate the inner coil 20 being curled within the body vessel 14. In at least one embodiment, the outer coil 18 has a pre-curled tension that is greater then the pre-curled tension of the inner coil 20. Consequently, along the length of the occluding device 10, a difference in pre-curled tension between the outer coil 18 and the inner coil 20 occurs at a transition or connection point 28. In one example, the inner coil 20 has a pre-curled tension of between about 5 to 60 grams of weight, and preferably between about 10 to 30 grams of weight. The outer coil 18 preferably has a pre-curled tension of between about 65 to 120 grams of weight, and preferably between about 75 to 100 grams of weight. The pre-curled tension (sometimes referred to as initial tension) may be defined to be the amount of force required to cause a 4 centimeter length of coil to begin to elongate. The pre-curled tension may also be defined by the amount of force required to cause a coil to begin elongating at a ratio of between about 1.25 to 15 grams per centimeter, and preferably between about 2.5 to 7.5 grams per centimeter. A coil having a pre-curled tension may be restrained substantially straight (see FIGS. 1a-2), e.g., for advancing through a catheter arrangement for deployment, reforming or recanalizing back to a coiled, looping or curled configuration when the restraining force is released. Without limiting the invention, it is believed that the pre-curled tension of the outer coil 18 provides a rigid support thereto to minimize migration of the device 10 within the lumen 12 and that the pre-curled tension of the inner coil 20 provides the occluding device 10 with the capability of being folded across (e.g. curled about or across) the diameter of the outer coil 18 within the lumen 12 after deployment from a catheter.

Alternatively, the inner coil 20 may be without a pre-curled tension. This embodiment may provide improved occlusion of the body vessel 14 in certain medical procedures. Without limiting the invention, it is believed that a minimally tensioned or non-tensioned soft inner-coil 20 may randomly fold upon itself in a non-predetermined fashion to more densely pack the outer coil 18, thereby enhancing occlusion of the body vessel 14.

As illustrated in FIGS. 3a and 3b, the occluding device 10 comprises the outer coil 18 which may form a first curled configuration 30 and the inner coil 20 which may form a second curled configuration 32. In at least one embodiment, the second curled configuration 32 is different than the first curled configuration 30. For example, the curled configurations 30 and 32 may form a series of loops 26 and 27, respectively. Preferably, the device 10 when curled into the first and second configurations 30 and 32 has a length between about 2 to 30 centimeters. Moreover, the series of loops 26 and 27 define corresponding cross-sectional lumens 38 (see FIG. 3c) formed axially along the length of the device 10. The loops from either series 26 and 27 are preferably spaced apart from adjacent loops by up to 5 millimeters of curl space. The series of loops 26 and 27 may respectively have uniform curl spaces and outside diameters 42 between each loop or alternatively, the curl spaces and outside diameters 42 may vary.

The occluding device 10 (i.e. the outer coil 18 and/or the inner coil 20) may include attached fibers 34 extending therefrom. The fibers 34 may be spaced apart from each other and held between wire windings 40 (also see FIG. 2) of the outer coil 18 and/or inner coil 20. Preferably, the fibers 34 include strands 36 comprising a synthetic polymer such as polyester textile fiber, e.g., DACRON™. As desired, the strands 36 may be positioned between adjacent loops, alternating loops, alternating double loops, or any desired configuration.

Preferably, the strands 36 have a length extending from the outer coil 18 and/or inner coil 20 between 5 to 6 millimeters as desired. In this embodiment, the fibers 34 are spaced apart from each other by about 1 to 2 millimeters. Preferably, the strands 36 have an outer diameter of about 0.00050 to 0.00100 inch.

Figure 3C:
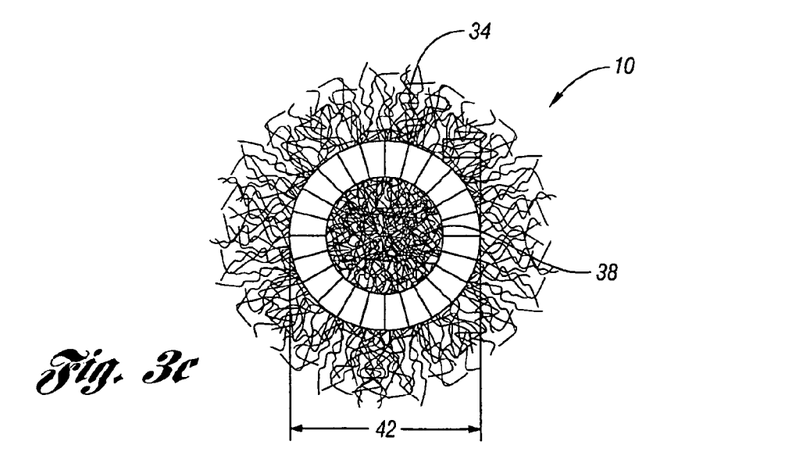
FIG. 3c is a longitudinal side view of an occluding device in accordance with one embodiment of the present invention.

FIG. 3c illustrates an end view of the occluding device 10 in a curled configuration. The curled occluding device 10 may have an outside diameter 42 ranging from about 3 to 15 millimeters. In at least one embodiment, the outer coil 18 of the occluding device 10 has a greater outside diameter 42 than the inner coil 20. Preferably, the outside diameter 42 of the outer coil 18 provides greater rigidity or radial force which facilitates retention of the device 10 along the inner wall 16 of the body vessel 14. In high blood flow body vessels, such as for example, major arteries or arteries feeding veins, the high radial force of the outer coil 18 promotes retention of the occluding device 10 therein. The smaller outside diameters 42 of the inner coil 20 preferably allows the inner coil 20 to pack the curled outer coil 18 to facilitate occlusion of the body vessel 14.

In one embodiment, the occluding device 10 may comprise at least one or more metals and/or metal alloys which may result in variable rigidity along the length of the device 10. For example, the device 10 may comprise platinum and platinum alloys. In another example, the outer coil 18 may comprise at least one of stainless steel, Inconel alloy (Ni—Cr alloy), platinum, platinum alloy, and palladium. The inner coil 20 may comprise at least one of platinum, platinum alloy, palladium, and palladium alloy. In this example, the inner coil 20 is made of a less rigid material than the outer coil 18.

In another embodiment, the outer coil 18 may have a tensile strength of between about 200,000 and 400,000 pounds per square inch and the inner coil 20 may have a tensile strength of between about 50,000 and 350,000 pounds per square inch. It has been determined that the tensile strength ranges described above provides the inner coil 20 with the capability of being flexible, malleable, and folded and provides the outer coil 18 with sufficient radial force to anchor the device 10 within the body vessel 14. Furthermore, the tensile strength differential between the inner coil 20 and the outer coil 18 may facilitate occlusion of the body vessel 14.

The device 10 may be made of other suitable materials including a super elastic material, cobalt-chromium-nickel-molybdenum-iron alloy, or cobalt-chrome alloy. It is understood that the device 10 may also be formed of any suitable material that will result in a self-opening or self-expanding device, such as shape memory materials. Shape memory materials or alloys have the desired property of becoming rigid, i.e., returning to a remembered state, when heated above a transition temperature. A shape memory alloy suitable to the present invention is Ni—Ti available under the more commonly known name Nitinol. When this material is heated above the transition temperature, the material undergoes a phase transformation from martensite to austenite, such that the material returns to its remembered state. The transition temperature is dependent on the relative proportions of the alloying elements Ni—Ti and the optional inclusion of alloying additives.

In one example, the device 10 may be made of Nitinol with a transition temperature which is slightly below normal body temperature of humans, which is about 98.6° F. Thus, when the device 10 is deployed in a body vessel 14 and exposed to normal body temperatures, the alloy of the device 10 will transform to austenite, that is, the remembered state, which for one embodiment of the present invention is the expanded state when the device 10 is deployed in the body vessel 14. To remove the device 10 it is cooled to transform the material to martensite which is more ductile than austenite, making the device 10 more malleable. As such, the device 10 can be more easily collapsed and pulled into the lumen of a catheter for removal.

In another example, the device 10 may be made of Nitinol with a transition temperature that is above normal body temperature of humans. Thus, when the device 10 is deployed in the body vessel and exposed to normal body temperature, the device 10 is in the martensitic state so that the device 10 is sufficiently ductile to bend or form into a desired shape, e.g., the inner coil 20 being folding across the outer coil 18 to occlude the body vessel 14. To remove the device 10, the device 10 is heated to transform the metal to austenite so that it will become rigid and returns to a remembered state.

In at least one embodiment, the outer coil 18 is attached to the inner coil 20. Some example processes for attaching the coils 18 and 20 are adhesive bonding, soldering, welding, rotational engagement of the wire windings 40 of the inner coil 20 with the outer coil 18, friction connection, compression fit, and crimping. However, any other suitable processes known in the art for attaching coils may also be used.

Without limiting the invention, FIGS. 5a through 5g illustrate several example configurations for the occluding device 10. FIG. 5a shows the occluding device 10 with an outer coil 18 disposed about an end portion 24 (end portion 24 illustrated in FIGS. 1a and 1b) of the inner coil 20. The outer coil 18 has a central axis 44 that is coincident with the central axis 46 of the inner coil 20. However, the central axes 44 and 46 may be parallel or positioned at angles to each other. The outer coil 18 and the inner coil 20 have regularly occurring loops 26 and 27 formed respectively by the coils 18 and 20. In this example, the outer diameter of the series of loops 26 of the curled outer coil 18 have a uniform diameter, whereas the series of loops 27 formed by the inner coil 20 have a variable diameter that is configured to taper distally from the outer coil 18 along the length of the inner coil 20.

FIG. 5b also illustrates an outer coil 18 and an inner coil 20 with coincident central axes 44 and 46. Moreover, both the outer and inner coils 18 and 20 have regularly occurring loops 26 and 27 with corresponding uniform diameters. Here, however, the inner coil 20 extends through a lumen formed by the series of loops 26 of the outer coil 18.

FIG. 5c illustrates the central axis 44 of the outer coil 18 being substantially transverse to the central axis 46 of the inner coil 20. It is understood, however, the central axes 44 and 46 may form any angle and/or be oriented substantially planar or non-planar with respect to each other.

FIG. 5d shows the outer coil 18 disposed about a substantially central portion of the inner coil 20. In this example, the inner coil 20 extends in opposing directions from the outer coil 18. Also, the corresponding series of loops 27 of the inner coil 20 have variable diameters which are configured to taper outwardly from the outer coil 18 along the length of the inner coil 20.

Figure 5E:
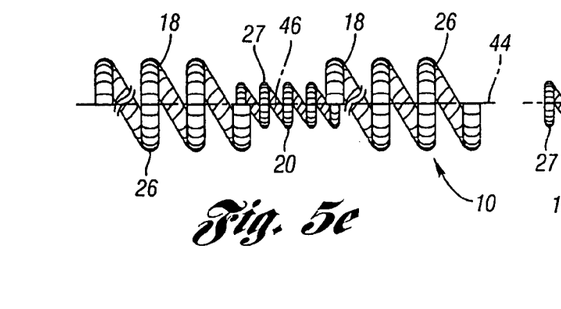
FIG. 5e is a side view of an occluding device in accordance with yet another embodiment of the present invention.

The device 10 shown in FIG. 5e has two outer coils 18, each disposed about an opposing end 24 of the inner coil 20. In this example, the outer coils 18 extend distally from the inner coil 20 with coincident central axes 44 and 46.

Figure 5F:
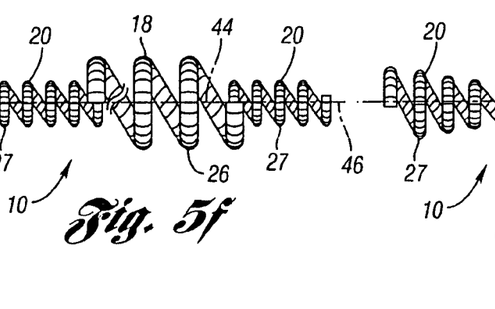
FIG. 5f is a side view of an occluding device in accordance with an embodiment of the present invention.

The device 10 depicted in FIG. 5f is configured similar to the device 10 shown in FIG. 5d except the series of loops 27 of the inner coil 20 are configured with a constant outside diameter.

Figure 5G:
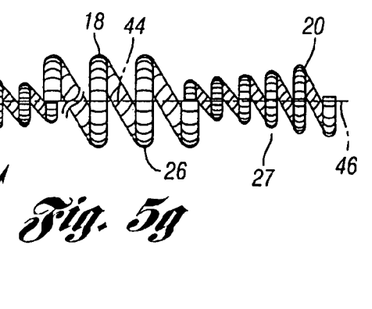
FIG. 5g is a side view of an occluding device in accordance with yet another embodiment of the present invention.

The device 10 depicted in FIG. 5g is also configured similar to the device 10 shown in FIG. 5d except the series of loops 27 of the inner coil 20 have a variable diameter which are configured to flare outwardly from the outer coil 18 along the length of the inner coil 20.

Figure 6A:
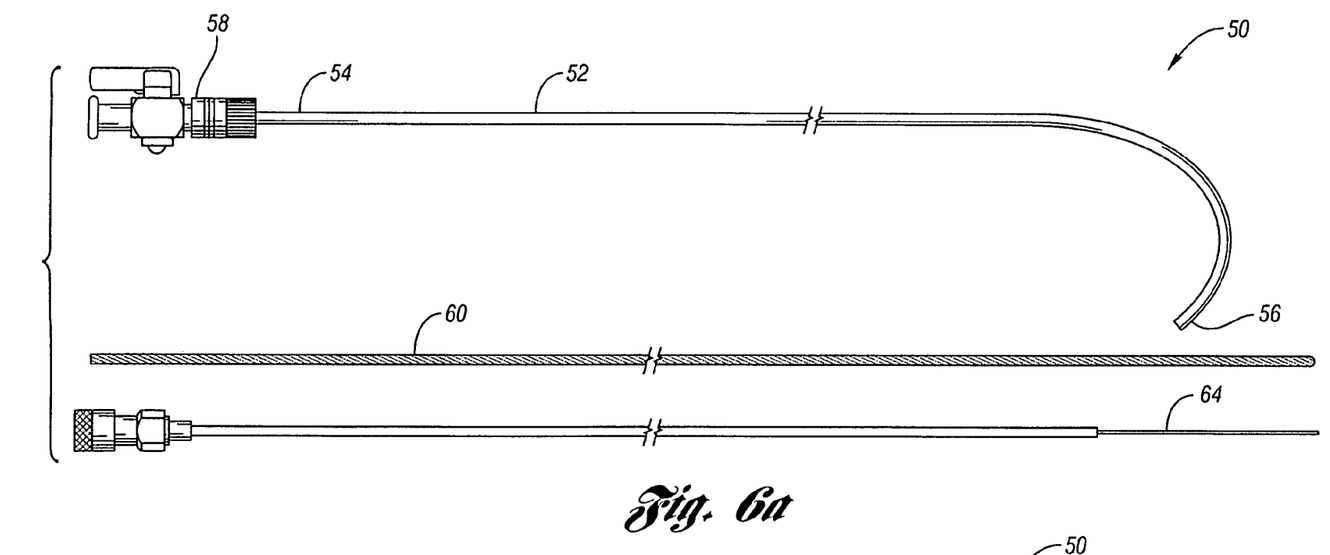
FIG. 6a is an exploded view of an embolization kit for the occluding device in accordance with one embodiment of the present invention.
Figure 6B:
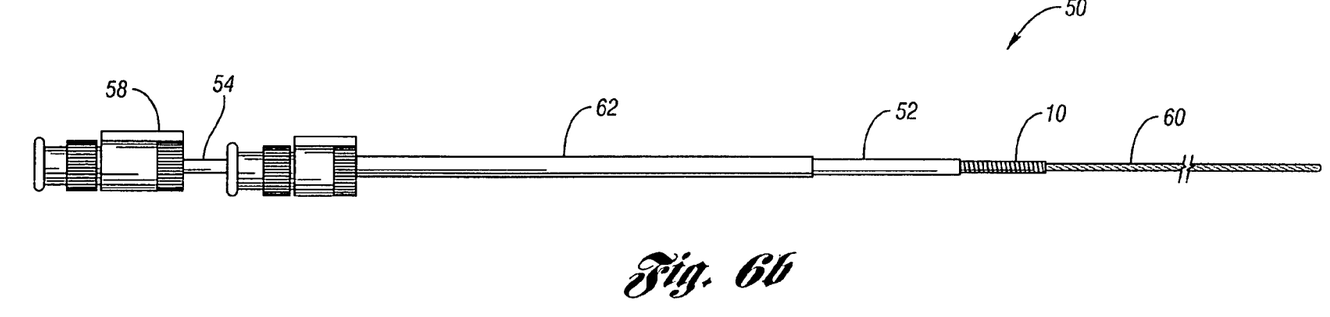
FIG. 6b is a side view of an embolization kit in accordance with an embodiment of the present invention.

FIGS. 6a and 6b illustrate an embolization kit 50 which implements the occluding device 10 in accordance with one embodiment of the present invention. As shown, the kit 50 includes a microcatheter 52 preferably made from a soft, flexible material such as silicone or any other suitable material. Generally, the microcatheter 52 has a proximal end 54, a distal end 56, and a plastic adapter or hub 58 to receive the device 10 to be advanced therethrough. In this embodiment, the inside diameter of the microcatheter 52 may range between 0.014 and 0.027 inch. The kit 50 further includes a guide wire 60 which provides a guide catheter 62 (discussed in more detail below) a path during insertion of the guide catheter 62 within the body vessel 14. The size of the wire guide 60 is based on the inside diameter of the guide catheter 62.

The kit 50 further includes a polytetrafluoroethylene (PTFE) guide catheter 62 or sheath for percutaneously introducing the microcatheter 52 into a body vessel 14. Of course, any other suitable material may be used without falling beyond the scope or spirit of the present invention. The guide catheter 62 may have a size of between about 4-French to 8-French and allows the microcatheter 52 to be inserted therethrough to a desired location in the body vessel 14. The guide catheter 62 receives the microcatheter 52 and provides stability of the microcatheter 52 at a desired location within the body vessel 14 (also refer to FIG. 4). For example, the guide catheter 52 may stay stationary within a common visceral artery, e.g., a common hepatic artery, and adds stability to the microcatheter 52 as the microcatheter 52 is advanced through the guide catheter 62 to a point of occlusion in a connecting artery, e.g., the left or right hepatic artery.

When the distal end 56 of the microcatheter 52 is at the point of occlusion in the body vessel 14, the occluding device 10 is loaded at the proximal end 54 of the microcatheter 52 and is advanced through the microcatheter 52 for deployment through the distal end 56. In this embodiment, a pushwire 64 is used to mechanically advance or push the occluding device 10 through the microcatheter 52. The size of the pushwire 64 used depends on the diameter of the microcatheter 52. As mentioned above, when the device 10 is deployed in the body vessel 14, the outer coil 18 serves to hold the device 10 in place along the inner wall 16 of the body vessel 14 and the inner coil 20 and the fibers 34 serve to occlude fluid flow by filling the lumen 12 of the body vessel 14.

In an alternative embodiment, an elongated releasing member (not shown) made be used instead of a pushwire 64. The elongated releasing member is similar to the pushwire 64 in that it may be advanced through the microcatheter 52 to deploy the device 10 through the distal end 56. However, the elongated releasing member further includes a distal end configured for selectively engaging and/or disengaging with the device 10. For example, the distal end of the elongated releasing member may have threads which engage with the wire windings 40 of the device 10. Once the device 10 is deployed through the microcatheter 52, the elongated releasing member may be twisted or un-screwed to disengage the device 10 from the elongated releasing member, thus releasing the device 10 within the body vessel 14. Other suitable releasing devices known to those skilled in the art may also be used to advance and selectively deploy the occluding device 10 from the microcatheter 52.

It is to be understood that the body cavity embolization kit 50 described above is merely one example of a kit that may be used to deploy the occluding device 10 in a body vessel 14. Of course, other kits, assemblies, and systems may be used to deploy any embodiment of the occluding device without falling beyond the scope or spirit of the present invention.

Figure 7:
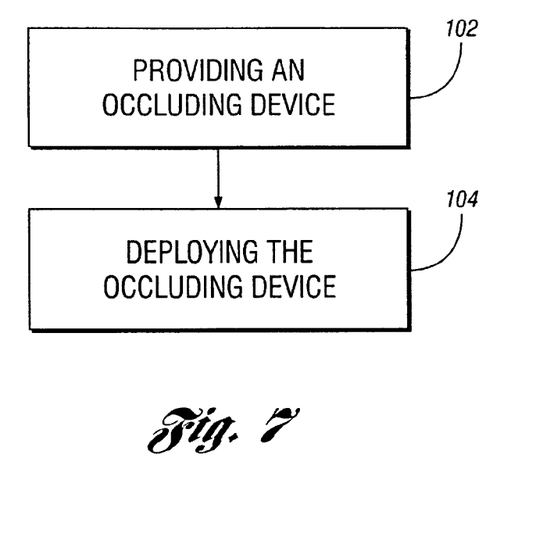
FIG. 7 is a flowchart for a method of occluding fluid flow through a body vessel in accordance with one example of the present invention.

FIG. 7 illustrates a method of occluding fluid flow through a body vessel in accordance with at least one embodiment of the present invention. The method comprises providing an occluding device 102. The occluding device includes an inner coil and an outer coil disposed about a portion of the inner coil. The outer coil has a pre-curled tension to facilitate the outer coil to be curled. The occluding device is deployed 104 into the lumen of a body vessel. Deployment of the occluding device includes deploying the outer coil at a desired point of occlusion in the body vessel. The outer coil curls to hold the occluding device in place within the body vessel. The inner coil is deployed across the lumen of the body vessel adjacent to the outer coil to pack the outer coil and occlude the body vessel.

As a person skilled in the art will readily appreciate, the above description is meant as an illustration of the implementation of the principles of this invention. This description is not intended to limit the scope of application of this invention in that the invention is susceptible to modification, variation, and change, without departing from the spirit of this invention, as defined in the following claims.

The invention claimed is:

1. An occluding device for occlusion of fluid flow through a lumen of a body vessel, the device comprising:
    an inner coil having first primary curls that define a first primary lumen; and
    at least one outer coil having second primary curls that define a second primary lumen that is coaxial with the first primary lumen, the at least one outer coil being disposed about only a portion of the inner coil, the inner coil having a first pre-curled tension between about 5 to 60 grams of weight and the outer coil having a second pre-curled tension greater than the first pre-curled tension to facilitate the outer and inner coils to be curled into first and second secondary configurations within the lumen of the body vessel when deployed, the at least one outer coil being more rigid than the inner coil.

2. The device according to claim 1 wherein the second pre-curled tension is between about 65 to 120 grams of weight.

3. The device according to claim 1 wherein the second configuration is different than the first configuration.

4. The device according to claim 3 wherein the second configuration extends from the first configuration in a first direction and has a viable outside diameter configured to one of flare and taper in the first direction along a length of the inner coil.

5. The device according to claim 3 wherein the first and second configurations correspondingly have a first series of loops axially spaced apart by up to about 5 millimeters curl space and a second series of loops axially spaced apart by up to about 5 millimeters curl space.

6. The device according to claim 5 wherein the first and second series of loops are correspondingly formed about a first central axis and a second central axis substantially parallel with the first central axis.

7. The device according to claim 5 wherein the first and second series of loops are correspondingly formed about a first central axis and a second central axis substantially non-parallel with the first central axis.

8. The device according to claim 1 wherein the at least one outer coil includes at least two outer coils disposed about respective portions of the inner coil.

9. The device according to claim 1 wherein the outer coil includes at least one of stainless steel, Inconel alloy, platinum, platinum alloy and palladium and the inner coil includes at least one of platinum, platinum alloy, palladium and palladium alloy.

10. The device according to claim 1 wherein the first pre-curled tension is between about 10 to 30 grams of weight and the second pre-curled tension is between about 75 to 100 grams of weight.

11. The device according to claim 1 wherein the outer coil is attached to the inner coil by one of adhesive bonding, soldering, welding, winding engagement, friction connection, compression fit and crimping.

12. The device according to claim 1 further comprising fibers attached to at least one of the inner and outer coils and extending therefrom.

13. An occluding device for occlusion of fluid flow through a lumen of a body vessel, the device comprising:
    an inner coil having first primary curls that define a first primary lumen; and
    at least one outer coil having second primary curls that define a second primary lumen that is coaxial with the first primary lumen, the at least one outer coil being disposed about only a portion of the inner coil, the inner coil having a first pre-curled tension that is minimal or zero and the at least one outer coil having a first second pre-curled tension greater than the first pre-curled tension to facilitate the outer and inner coils to be curled into first and second secondary configurations within the lumen of the body vessel when deployed, the at least one outer coil being more rigid than the inner coil.

14. The device according to claim 13 wherein the second pre-curled tension is between about 65 to 120 grams of weight.

15. The device according to claim 13 wherein the second pre-curled tension is between about 75 to 100 grams of weight.

16. An embolization kit for occluding fluid flow through a body vessel, the kit comprising:
- an occluding device including:
  - an inner coil having first primary curls that define a first primary lumen; and
  - at least one outer coil having second primary curls that define a second primary lumen that is coaxial with the first primary lumen, the at least one outer coil being disposed about only a portion of the inner coil, the at least one outer coil having a first pre-curled tension between about 65 to 120 grams of weight and the inner coil having a second pre-curled tension less than about 60 grams of weight to facilitate the outer and inner coils to be curled into first and second secondary configurations within the lumen of the body vessel when deployed;
- a guide catheter; and
- a microcatheter configured to be passed through the guide catheter to position the microcatheter in the body vessel and to deploy the occluding device.

17. The kit according to claim 16 wherein the first pre-curled tension is between about 10 to 30 grams of weight and the second pre-curled tension is between about 75 to 100 grams of weight.

18. The kit according to claim 16 wherein second pre-curled tension is between about 5 to 60 grams of weight.

19. The kit according to claim 16 further comprising one of a pusher wire and an elongated releasing member for advancing the occluding device.

20. The kit according to claim 16 further comprising a guide wire for guiding the guide catheter in the body vessel.

21. A method of occluding fluid flow through a lumen of a body vessel, the method comprising:
- deploying an occluding device into the lumen of the body vessel, the occluding device including an inner coil having first primary curls that define a first primary lumen, the occluding device further including and at least one outer coil having second primary curls that define a second primary lumen that is coaxial with the first primary lumen, the at least one outer coil being disposed about only a portion of the inner coil, the outer coil having a first pre-curled tension between about 65 and 120 grams of weight and the inner coil having a second pre-curled tension less than about 60 grams of weight to facilitate the outer and inner coil to be curled into first and second secondary configurations, and wherein deploying the occluding device includes:
  - deploying the outer coil at a desired point of occlusion in the body vessel, the outer coil curling to hold the occluding device in place within the body vessel; and
  - deploying the inner coil across the lumen of the body vessel adjacent to the outer coil to pack the outer coil and occlude the body vessel.

\* \* \* \* \*

UNITED STATES PATENT AND TRADEMARK OFFICE
CERTIFICATE OF CORRECTION

| | | |
|---|---|---|
| PATENT NO. | : 8,702,746 B2 | Page 1 of 1 |
| APPLICATION NO. | : 12/111474 | |
| DATED | : April 22, 2014 | |
| INVENTOR(S) | : Tekulve et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1579 days.

Signed and Sealed this
Twenty-first Day of July, 2015

Michelle K. Lee
*Director of the United States Patent and Trademark Office*